United States Patent [19]

Perciaccante et al.

[11] 4,047,533

[45] Sept. 13, 1977

[54] ABSORBABLE SURGICAL SUTURES COATED WITH POLYOXYETHYLENE-POLYOXYPROPYLENE COPOLYMER LUBRICANT

[75] Inventors: Vincent Anthony Perciaccante, Long Island City; Henry Patrick Landi, Yorktown Heights, both of N.Y.

[73] Assignee: American Cyanamid Company, Stamford, Conn.

[21] Appl. No.: 724,804

[22] Filed: Sept. 20, 1976

[51] Int. Cl.$^2$ ............................................. A61L 17/00
[52] U.S. Cl. ............................... 128/335.5; 128/1 R; 428/375
[58] Field of Search .................. 128/1, 335.5; 428/275

[56] References Cited

U.S. PATENT DOCUMENTS

| | | | |
|---|---|---|---|
| 3,061,470 | 10/1962 | Kuemmerer | 428/375 X |
| 3,432,898 | 3/1969 | Stanley et al. | 428/396 X |

Primary Examiner—Leland A. Sebastian
Attorney, Agent, or Firm—Charles F. Costello, Jr.

[57] ABSTRACT

The handling characteristics, including particularly the knot run-down, of synthetic absorbable surgical sutures and tissue drag characteristics are improved by a coating of a lubricating film of a bioabsorbable copolymer having polyoxyethylene blocks and polyoxypropylene blocks, and which bioabsorbable copolymer has a molecular weight such that it is pasty to solid at 25° C.

23 Claims, 2 Drawing Figures

ABSORBABLE SURGICAL SUTURES COATED WITH POLYOXYETHYLENE-POLYOXYPROPYLENE COPOLYMER LUBRICANT

BACKGROUND OF THE INVENTION

The handling characteristics of surgical sutures encompass many factors, some of which factors are at least in part inconsistent or seemingly inconsistent. There is a constant effort to improve the handling characteristics. Among the more important of the handling characteristics are those associated with knot rundown. In many surgical procedures it is necessary that a knot be tied in a suture when the knot is deep inside a surgical or natural opening. For instance, a dental surgeon may need to tie a knot inside a patients mouth. An intravaginal hysterectomy requires suturing in restricted quarters. One technique frequently used is to tie a square knot that can be run-down from an exterior location where the knot is first tied to lie against tissue with a desired degree of tightness. The knot is snugged down so that it is holding with a degree of firmness chosen by the surgeon for a particular situation and then additional throws are tied down against the first throws of the square knot. In some instances, the first throw is a double twist followed by a single throw to form a surgeons knot, with additional throws to form additional square knots on top as needed. As contrasted with the ease of placement, is the necessity of knot security. Each though it is desired that it be easy to tie a knot, it is mandatory that the knot hold without slipping for an acceptable length of time. With buried absorbable sutures, of course, the suture including the knot is eventually absorbed, and the knot need only hold until the tissue is adequately regenerated. This can be merely a few hours for certain types of skin incisions, up to requirements of the order of 15 to 28 days for many types of internal knots. If strength for a longer time or permanent reinforcement is needed, non-absorbable sutures may be used.

Some suture materials are so smooth that a knot runs down very readily and frequently becomes readily untied. Other sutures are of materials in which the knot tends to "lock-up" or refuse to run-down so that it is difficult to snug-down the throws against the tissue and only a few throws are needed, and security is not a problem. Knots in constantly moving tissue, such as adjacent to the heart, have a much greater chance of becoming untied than knots in quiescent tissue such as knots holding together a wound inside a plaster cast.

The problem of improving suture performance under varied conditions has been the subject of much research over a prolonged period.

PRIOR ART

U.S. Pat. No. 1,254,031 — Jan. 22, 1918, Davis, SUTURE AND METHOD OF MAKING THE SAME, shows a braided collagen suture immersed in collagen or glue to cause close adhesion of the braid, to fill up the interstices and provide a smooth uniform coating.

U.S. Pat. No. 2,576,576 — Nov. 27, 1951, Cresswell and Johnstone, LUBRICATED THREAD, shows a lubricated multifilament collagen thread using as a lubricating film a phosphatide such as lecithin. The lecithin should be applied at the time of coagulation or regeneration of collagen as effective lubrication is not obtained if the lubricant is incorporated by adding to a finished thread.

U.S. Pat. No. 2,734,506 — Feb. 14, 1956 - Nichols et al. SILK SUTURES AND LIGATURES shows using poly(alkyl methacrylate) as a coating for silk sutures, and a hot coating die system.

U.S. Pat. No. 3,187,752 — June 8, 1956 — Glick, NON-ABSORBABLE SILICONE COATED SUTURES AND METHOD OF MAKING, shows silk or other non-absorbable synthetic filaments such as nylon, cotton or linen coated with a silicone which gives a more inert suture and reduces capillarity.

U.S. Pat. No. 3,209,589 — Oct. 5, 1965 — Schlatter, YARN FRICTION MEASURING INSTRUMENT, describes a machine for measuring the friction of a yarn sliding over itself and describes the variation of friction with speed, and the "slip-stick" variety at slow speeds.

U.S. Pat. No. 3,297,033 — Jan. 10, 1967 - Schmitt and Polistina, SURGICAL SUTURES, shows synthetic surgical sutures of polyglycolic acid and discloses that the surfaces of the fiber can be coated with a silicone, beeswax, or the like to modify the handling or the absorption rate.

U.S. Pat. No. 3,390,681 — July 2, 1968, Kurtz, POLYESTER SUTURE HAVING IMPROVED KNOTTING CHARACTERISTICS, shows improving the knotting characteristics of a polyester such as one formed from a dicarboxylic acid and a diol (Dacron) by depositing on the fibers a polytetrafluoroethylene (Teflon). This patent discloses many of the problems in suture knots, and is hereby incorporated by this reference thereto. This patent also shows the accepted practice of classing "ligatures" under "sutures" for patent disclosure purposes.

U.S. Pat. No. 3,565,077 — Feb. 23, 1971, Glick, DENSIFIED ABSORBABLE POLYGLYCOLIC ACID SUTURE BRAID, AND METHOD FOR PREPARING SAME, shows a suture construction using polyglycolic acid filaments with a compacted structure and a reduced void fraction.

U.S. Pat. No. 3,815,315, June 11, 1974, Glick, ETHYLENE OXIDE STERILIZATION OF MOISTURE SENSITIVE SURGICAL ELEMENTS shows the desirability of maintaining surgical elements of polymers subject to the hydrolytic degradation to non-toxic, tissue-compatible, absorbable components, such as polyglycolic acid sutures, in a desiccated condition in an air tight container impervious to moisture vapor. Suitable desiccating cycles and foil containers to give product which are storage stable for years are disclosed.

U.S. Pat. No. 3,867,190 — Feb. 18, 1975, Schmitt and Epstein, REDUCING CAPILLARITY OF POLYGLYCOLIC ACID SUTURES, shows the coating of polyglycolic acid surgical sutures with a copolymer of from 15-85% glycolic acid with 85-15% lactic acid which coating fills the interstices of a multi-filament polyglycolic acid suture. Example 10 discloses the coating as minimizing capillarity, and improving run-down. Thicker coatings increase stiffness. This patent has 38 references to earlier prior art on sutures and methods of making them, and related fields and is incorporated herein by this reference thereto. A divisional of said 3,867,190 is Ser. No. 489,004, July 16, 1974, REDUCING CAPILLARITY OF POLYGLYCOLIC ACID SUTURES, now U.S. Pat. No. 3,982,543 dated Sept. 28, 1976.

U.S. Pat. No. 3,896,814 — July 29, 1975 — Vivien and Schwartz, COLLAGEN BASED THREADS, shows a collagen or catgut thread which is flexibilized by having therein water and a hygroscopic agent such as a glycerol or a glycol or a low molecular weight (up to 400 m.w.) liquid polyalkalene oxide, and which may additionally be coated with a lipoid or a silicone for surface lubricity.

U.S. Pat. No. 3,942,532 — Mar. 9, 1976 — Hunter and Thompson — BRAIDED SUTURE, discloses an adaptation of an INSTRON Universal Testing Instrument using an oscillographic recorder, to use a single throw between two suture strands to measure surface roughness, as an indication of the ease of sliding a single throw knot down the suture into place, there called "tie-down performance". A coating of 0.4 percent to 7 percent of the suture weight of an aliphatic polyester such as a condensate of adipic acid and 1,4-butanediol having a molecular weight of about 2,000–3,000 is recommended.

U.S. Ser. No. 691,749, filed June 1, 1976 — Casey and Epstein — NORMALLY-SOLID BIOABSORBABLE, HYDROLYZABLE, POLYMERIC REACTION PRODUCT, discloses the use of transesterification product of poly(1,4-propylene diglycolate) and polyglycolic acid and other trans-esterification products of polyglycolic acid and a polyester of diglycolic acid and an unhindered glycol to coat sutures to improve knot run-down and other suture characteristics.

The coating, coloring and conditioning of surgical sutures with polymeric materials in general is well-known. Silicones, wax, polytetrafluoroethylene, and other polymers have been used. Specific coating materials with unique advantages to give improved sutures are constantly being sought.

SUMMARY OF THE INVENTION

It has now been found that the knot run-down characteristics, handleability, tie-down performance and tissue drag characteristics of braided, twisted or covered multifilament synthetic absorbable sutures may be improved by coating with a lubricating biologically absorbable copolymer having polyoxyethylene blocks and polyoxypropylene blocks.

Absorbable polyglycolic acid sutures are described in U.S. Pat. No. 3,297,033, supra. Other synthetic absorbable sutures which absorb in living tissue may be coated with improved results. At present absorbable sutures meeting with market acceptance are those in which the degradation or absorption in tissue results from the hydrolytic degradation of glycolic acid ester linkages. Such materials are presently being sold under the trademarks DEXON® and VICRYI®. The present invention may be used with other synthetic absorbable surgical sutures, described in the prior art, and as they are developed. With synthetic absorbable sutures the problem of a coating to improve knot run-down characteristics is made more difficult by the requirement that the coating must be non-toxic and absorbable.

Absorbable or bioabsorbable as applied to the coating, refers to a coating which by hydrolytic or enzymatic degradation, or by its inherent characteristic, has such molecular weight and solubility properties that it is absorbed from the surface of the suture and is eliminated by the subject either unchanged or in hydrolyzed or degraded form. The exact mechanism of the disposition of the coating in mammalian tissue is not critical to the understanding of the present invention, as long as the coating is non-toxic.

It is also found that the lubricant coating not only aids in the knot run-down characteristics but increases the smoothness and flexibility of the sutures so that they may be more easily drawn through the skin and other tissues during placement of the suture. This reduction in friction is called reduced tissue drag.

Another unexpected and unobvious advantage of the present lubricant coating in that the lubricant copolymers are absorbed from the suture within a few days. The coating that aids in friction reduction in tissue drag and lubricates in knot placement also causes the knot to slip more readily. When the lubricant is comparatively rapidly absorbed in living mammalian tissue, the resistance of the knot to slippage or untieing due to tissue movement is soon increased. As the wound heals the knot security actually improves, up to the time that the synthetic absorbable suture loses strength preliminary to absorption.

The absorbable coating is one or more of a group of compounds having blocks of polyoxyethylene and blocks of polyoxypropylene in their structure. For simplicity and ease of description these compounds are taught, drawn and treated as if there were merely two or three blocks in the chain. However, it is to be understood that non-significant qualities of polyoxypropylene may be present in the polyoxyethylene block and minor quantities of polyoxyethylene may be present in the polyoxypropylene block. From the methods of manufacture it would appear that there may be and probably are such minor admixtures present in the chain. The commercially available grades are acceptable and found to have a low and acceptable degree of toxicity.

The present lubricants may be indicated as having the formula:

where one of $R_1$ and $R_2$ is methyl and the other hydrogen, and $n$ and $m$ are sufficiently large that the compound is pasty to solid at 25° C., R is the residue of a relatively low molecular weight reactive hydrogen compound having from 2 to about 6 reactive hydrogen atoms and having not over 6 carbon atoms in said compound, and c is the number of reactive hydrogens on the compound forming R. Those compounds which are at least pasty at 25° C. are preferred because they adhere better to the synthetic absorbable polyfilamentary suture. There is not a sharp cut off, but in general as the materials become more pasty or solid, their effectiveness improves.

The lubricant compounds and methods of manufacture are described at length in certain prior art. The Pluronics in general are described in U.S. Pat. No. 2,674,619, Apr. 6, 1954, POLYOXYALKYLENE COMPOUNDS, L.G. Lundsted. These are referred to as a cogeneric mixture of conjugated polyoxypropylene-polyoxyethylene compounds and are further described therein.

Certain nitrogen containing polyoxyethylene detergent compositions which are here useful as lubricants are described in U.S. Pat. No. 2,979,528, Apr. 11, 1961, NITROGEN-CONTAINING POLYOXYALKYLENE DETERGENT COMPOSITIONS, L.G. Lundsted. Column 4, lines 44–58 of this patent disclose that the oxypropylene chains may have a small amount of ethylene-oxide therein and vice versa. Because of the sources of ethylene oxide and propylene oxide, usually from petroleum fractions, it is to be expected that in commercial practice complete rectification to chemically pure compounds is not obtained. Fortunately the commercial grade may be used on absorbable sutures with excellent results. Said 2,979,528 also points out that as polymers, all molecular species are far from identical—some chains are shorter, some are longer, but on the average the materials are as indicated and it is the physical properties of the lubricants, not the molecular weight spread of the components, which are important.

U.S. Pat. No. 3,036,118, May 22, 1962, MIXTURES OF NOVEL CoNJUGATED POLYOXYETHYLENE-POLYOXYPROPYLENE COMPOUNDS, D. R. Jackson and L. G. Lundsted, has much disclosure on the addition of polyoxyethylene groups and polyoxypropylene groups to reactive hydrogen compounds having from 2 to 6 reactive hydrogen atoms and not over 6 carbon atoms per molecule. Among other such compounds are listed the group consisting of aliphatic polyhydric alcohols, alkylamines, alkylene polyamines, cyclicamines, amides, and polycarboxylic acids, oxyethylene groups and oxypropylene groups. The reactive hydrogen compound serves as a chain initiator and can be present in such a small proportion that it has minor significance in its own right and serves mainly as a foundation on which the predominantly polyoxyethylene or polyoxypropylene blocks may be added in the chosen order. Whereas Patent 3,036,118 claims primarily the Reverse Pluronics in which the polyoxy-ethylene chains are attached to the nucleus or initiating reactive hydrogen compounds, in the present invention either the Reverse Pluronic with the polyoxyethylene in the center or the regular Pluronics with the polyoxypropylene in the center or the Tetronics with nitrogen in the center may be used for lubricant purposes.

Because the chemistry is previously known, and to avoid unnecessarily extending the length of the present disclosure, the disclosures of each of these three patents is herein hereby incorporated by this reference thereto.

These lubricating bioabsorbable copolymers are often classed as surface active agents as the polyoxyethylene blocks are predominantly hydrophylic and the polyoxypropylene blocks are predominantly hydrophobic. The materials have been sold by the Wyandotte Chemical Company under the trademark of PLURONICS for the formula:

where x, y and z are whole numbers. REVERSE PLURONICS for the formula:

where n, m and o are whole numbers and TETRONICS for the formula:

where R₁ is where q and r are whole numbers.

For the present purposes as synthetic absorbable suture lubricants, the values of x, y, z, n, m, o, q and r are such that the lubricants are pasty to solid at 25° C.

The pastes are opague semi-solids with melting points above room temperature—preferably above about 40° C.

Those classed as Pluronics are particularly useful for the present invention.

The physical characteristics of these lubricant compounds are affected by their total molecular weight and by the percentage of polyoxyethylene in the molecule. References are made to the commercially available compounds for purposes of convenience. Those which are liquid normally have an L as a primary designator, those which are pasty have a P and those which are solid have an F. For the Pluronics, the first number indicates the typical molecular weight of the polyoxypropylene hydrophobic portion with a number 3 being about 950; 4 being about 1200; 5 being about 1450; 6 about 1750; 7 about 2050; 8 about 2250; 9 about 2750; 10 about 3250; 11 about 3625 and 12 about 4000. The second digit indicates the approximate percentage of the polyoxyethylene hydrophylic units in the total molecular, in units of 10. Thus for example, the formulations of certain commercially available products is approximately that shown in Table I.

As all compositions are mixtures, all values are approximate, and values are subject to some rounding.

Additional data is given in The Journal of the American Medical Association, volume 217, pages 469 to 470 (1971) where the new nonproprietary name of POLOXAMER is established for these compositions as direct food additives.

TABLE I

| PLURONIC | Average Molecular Weight | M.W. of each Polyoxyethylene Block | Units of each x and z | % Polyoxyethylene | M.W. of Polyoxypropylene Block | Units of y | M.P. ° C. |
|---|---|---|---|---|---|---|---|
| F-38 | 5000 | 2000 | 46 | 80 | 930 | 16 | 45 |
| F-68 | 8350 | 3300 | 75 | 80 | 1,750 | 30 | 52 |
| F-77 | 6600 | 2300 | 52 | 70 | 2,050 | 35 | 48 |
| P-85 | 4600 | 1200 | 27 | 50 | 2,250 | 39 | 40 |
| F-87 | 7700 | 2700 | 62 | 70 | 2,250 | 39 | 49 |
| F-88 | 10800 | 4300 | 97 | 80 | 2,250 | 39 | 54 |
| F-98 | 13500 | 5400 | 122 | 80 | 2,750 | 47 | 55 |
| F-108 | 14400 | 5600 | 128 | 80 | 3,150 | 54 | 57 |

TABLE I-continued

| | | | | M.W. polyethylene units of m block | | M.W. polyoxypropylene block | Units of n and O |
|---|---|---|---|---|---|---|---|
| F-127 | 12500 | 4300 | 98 | 70 | | 3,900 | 67  56 |

| REVERSE PLURONIC | | | M.W. polyethylene units of m block | | M.W. polyoxypropylene block | Units of n and O | |
|---|---|---|---|---|---|---|---|
| 10R8 | 3,000 | 2000 | 45 | 65% | 562 | 9 | 46 |
| 17R8 | 4,350 | 2600 | 59 | 60% | 870 | 15 | 53 |
| 25R8 | 9,000 | 3250 | 74 | 57% | 1,250 | 22 | 56 |

| TETRONIC | Average Molecular Weight | Approximate Molecular Weight of Individual Polyoxyethylene Block | Approximate % Polyoxyethylene | Molecular Approximate Weight of Individual Polyoxypropylene Block | Approximate Polyoxypropylene | Average Approximate length of chains per block | |
|---|---|---|---|---|---|---|---|
| | | | | | | Units of r | Units of q |
| 707 | 12,000 | 2312 | 74 | 673 | 26 | 52.5 | 11 |
| 908 | 26,100 | 5588 | 85 | 923 | 15 | 127 | 15.9 |
| 1107 | 14,500 | 2438 | 67 | 1173 | 33 | 55.4 | 20.2 |
| 1307 | 18,600 | 3213 | 69 | 1423 | 31 | 73 | 24.5 |
| 1508 | 27,000 | 5063 | 75 | 1673 | 25 | 115 | 28.5 |

In general, the Pluronics with a molecular weight range of from about 4,750 to 16,250 are waxy solids. The polyoxypropylene portion has a molecular weight of 950 to 4,000 and the polyoxyethylene content of about 60–80%.

The pastes in general have a total molecular weight ranging from 3,500 to 5,700 with a polyoxypropylene molecular weight range of 1,750 to 6,500 and polyoxyethylene content of 30 to 50%. The transitions from wax to paste to liquid are not sharp.

COATING

The synthetic absorbable suture is conveniently coated by several conventional procedures including:

Melt Coating

The uncoated suture is placed in a split die whose orifice corresponds to diameter specifications for the particular size suture to be coated. The die is then clamped in a heating block and the polyoxyethylene-polyoxypropylene lubricant bioabsorbable copolymer placed in the die. The die is raised to a temperature about 20° C. above the melting point of said copolymer and after the copolymer has melted, the suture to be coated is slowly pulled downward through the molten material in the die and collected on a take-up spool. The spool is mounted directly below the die a sufficient distance to allow solidification of the coating. A cooling tunnel or a blast of cooling air may be used to increase production speeds. Nichols et al. 2,734,506, supra, describes one useful apparatus for coating.

Solution Coating

The polyoxyethylene-polyoxypropylene lubricant bioabsorbable copolymer is dissolved in chloroform. About twice the percentage by weight is used for coating solution as is desired on the final sutures. A feed loop such as a loop of wire or a ceramic is threaded with the uncoated suture, after which the feed loop is then submerged in the solution and the suture is passed down through the feed loop. It may be passed through a die whose diameter is such that after drying a suture will have the desired diameter. The suture is pulled slowly through the solution and at least partially dried in a drying tunnel. The drying is finished after the suture is wound on a spool. Because variations in equipment, speed, and temperature affect the pick-up of the lubricant bioabsorbable polymer, the concentration in the coating is adjusted based on a preliminary run or experience.

During the following the application of the coating to the synthetic absorbable sutures, contact of the filaments with moisture, or water vapor is minimized. The final coated suture is thoroughly dessicated before packaging in a moisture proof container, such as a metal foil envelope, for long term storage stability. U.S. Pat. No. 3,814,315 supra, discloses methods of dry packaging and sterilizing, and is hereby herein incorporated by this reference thereto.

Other coating techniques which are well known in the coating of polyfilamentary strands may be used. The techniques used for insulating wire may be adapted for large scale suture manufacture. The above are merely two of the more convenient and well known methods for coating. Details are later illustrated in examples.

Toxicity

The low toxicity of the polyoxyethylene-polyoxypropylene compounds of the present invention are shown in such U.S. Pat. Nos. as 3,450,502 which describes the use of a copolymer having a total molecular weight of about 8,750 in isotonic solutions used as a priming agent in a heart-lung apparatus. In sutures even if a maximum of around 25–30% by weight of the suture of copolymer is used, only a very small amount is placed in the subject.

The low toxicity is shown in the following table.

TABLE II

| | TOXICITY | | |
|---|---|---|---|
| Pluronic No. | Total Molecular Weight | Physical Characteristic | LD 50 (gm/kg) in Mice |
| F-38 | 5000 | wax | > 5 |
| F-77 | 6600 | wax | 4.2 |
| F-87 | 7700 | wax | 3.75 |
| F-68 | 8350 | wax | > 5 |
| F-88 | 10800 | wax | > 5 |
| F-127 | 12500 | wax | 2.25 |
| F-98 | 13500 | wax | > 5 |
| F-108 | 14400 | wax | 1.25 |
| P-65 | 3400 | paste | 0.83 |
| P-84 | 4200 | paste | 0.4 |
| P-85 | 4600 | paste | 0.53 |
| P-94 | 4600 | paste | 0.6 |
| P-103 | 4950 | paste | 1.4 |
| P-104 | 5850 | paste | 0.75 |
| P-123 | 5750 | paste | 2.7 |
| P-105 | 6500 | paste | 3 |

The polyoxyethylene-polyoxypropylene compositions used as the lubricant bioabsorbable copolymers have been used in food products; and have been the subject of studies as to their elimination from a mammalian body. In general, they are eliminated in the urine fairly rapidly, and within 48 hours nearly all have been eliminated from the blood stream.

If some of the lubricant bioabsorbable copolymer is trapped in braid pores of a suture, the rate of diffusion into the blood stream may be reduced and hence the time for elimination somewhat increased. The molecular weight is small enough that the lubricant bioabsorbable copolymers may be eliminated unchanged, although some degradation may occur before elimination. The important thing is that the lubricant bioabsorbable copolymer has no deleterious effect upon healing tissues adjacent to the sutures, and being removed from the surface of the suture by absorption by the body, knot security is improved. As soon as suture placement is completed, the knot run down and tissue drag reduction function is complete, and as the lubricant bioabsorbable copolymer is removed from the suture, knot security improves.

Definitions in the suture and textile trades are sometimes ambiguous or confused. As herein used;

A "filament" is a single, long, thin flexible structure of a non-absorbable or absorbable material. It may be continuous or staple.

"Staple" is used to designate a group of shorter filaments which are usually twisted together to form a longer continuous thread.

An absorbable filament is one which is absorbed, that is digested or dissolved, in living mammalian tissue.

A "thread" is a plurality of filaments, either continuous or staple, twisted together.

A "strand" is a plurality of filaments or threads twisted, plaited, braided, or laid parallel to form a unit for further construction into a fabric, or used per se, or a monofilament of such size as to be woven or used independently.

The term "suture" is used to include the term "ligature" as technically a suture is used with a needle whereas the ligature is merely used to tie without being placed by a needle.

A finished suture has a needle attached and is sterile and ready for use in surgery. For purposes of convenience in nomenclature, the term "suture" is frequently used to refer to the same strand before it is coated and before it is packaged and sterilized. Context indicates whether it is the sterile suture ready for use, or the suture in a manufacturing step which is referred to.

The strand of the suture is used as the basis for weight in determining the quantity of material that is placed on the synthetic absorbable polymer strand in forming the absorbable surgical suture.

The quantity of the lubricating bioabsorbable copolymer is from about 0.1 to 25 percent by weight of the lubricating bioabsorbable copolymer based on the weight of the uncoated strand forming the suture. It is not necessary that the coating be continuous as a discontinuous coating on the surface aids in reducing friction and chatter. A larger quantity may be present if the lubricating bioabsorbable copolymer penetrates inside the strand, with the various filaments themselves being partially or totally covered.

The wide range of coating weight permits adaptation of the present sutures to many varied uses. Because the strand to be coated to form the suture may have considerable variation in surface roughness, due to the mechanical structure, i.e. braid or twist, etc. as well as being made from filaments which are less than 2 denier per filament to more than 6 denier per filament, with the finer filament sizes giving a smoother surface; and because the filaments may be stretched after the suture is manufactured or in heat treatment, the surface roughness basically can vary. The smoother surfaces require less of the lubricating bioabsorbable copolymer for analogous degrees of slippage.

The various surgical techniques used interact with the desired degree of lubrication. For any given type of knot, a larger quantity of lubricant which for a particular technique increases the ease of run-down, also increases the ease of the knot running back or slipping, called knot security. For some surgical procedures it is highly desirable that the knot be very free in running down, even though the knot slips more readily.

A surgeon in tying knots is confronted with the interaction between the method of tying the knot and the ease of slipping. If a suture is comparatively well lubricated, the surgeon can use a square knot, which is run down readily; with additional squared throws for knot security. On the other hand, if the suture is less well lubricated, the surgeon can use a double half-hitch or some other type of knot which moves more readily to run the knot down to position, after which the double half hitch can be pulled to square the knot, or additional throws can be thrown down against the knot to give adequate knot security. Thus the surgeon can either adapt his knot technique to a particular suture, or can get sutures whose surface lubricity is best adapted to the technique which the surgeon desires to use. Generally, there is an adaptation of each to the other. The surgeon attempts to get a suture whose characteristics are those which he prefers, and then adapts his knot tying techniques to the sutures that he has at the time. Some surgeons make very successful knots with stainless steel wire using a knotting technique that is adapted to such a wire which has very poor run-down. Others prefer a much more readily run-down well-lubricated suture.

Additionally the location of use has influences. Sometimes a suture in passing through tissue picks up tissue fluids. The suture may be coated with tissue fluids which are either fresh or partly dry at the time the knot is tied. In some surgical techniques it is necessary to preplace the sutures, and tie the suture after the coating of tissue fluids on the suture has a chance to become at least partially dried.

Because the ease of knot run-down and knot security are somewhat opposite, it is necessary for the surgeon to use additional throws or such knots as will hold under the particular conditions of a selected surgical procedure. By changing the quantity of the lubricant bioabsorbable copolymer, the run-down can be modified to suit a using surgeons preference.

The time of use of the knots can be quite varied. Some surgeons use a suture to ligate bleeders in a wound with a retention requirement of 30 minutes or less. Such knots can be removed as the surgical procedure is complete, and before wound closure. Others leave the absorbable knots in the tissue even though there is no likelihood that a bleeder would reopen. For such usage, a suture which retains strength for 30 minutes is adequate. For wound closure and some other uses, it is desired that the synthetic absorbable suture maintain strength for at least 15 days to 4 weeks.

Because the present lubricating bioabsorbable copolymer is removed from the suture in living tissue, as the lubricant is removed the knot security increases and after 48 hours more or less, knot security is greatly improved.

The examples following should show the effects of certain different coating and quantities under certain conditions.

The requirements of surgery are extremely varied, and various coating weights permit adaptation of synthetic absorbable sutures to different conditions.

In general, if the surgeon desires a better lubricated suture, a larger quantity of the lubricating bioabsorbable copolymer is used and conversely if the surgeon in willing to accept slightly reduced knot run-down and tissue drag characteristics in favor of greater knot security, the coating level is reduced in favor of this particular compromise.

Usually from 2 percent to 8 percent of the lubricant bioabsorbable copolymer gives a useful range of compromise between the ease of knot run-down and knot security.

A usage of about 5 percent by weight of Pluronic F-68 is a preferred compromise between the knot run-down and knot security requirements for 2 to 6 denier per filament braided sutures of polyglycolic acid.

Figure 1:
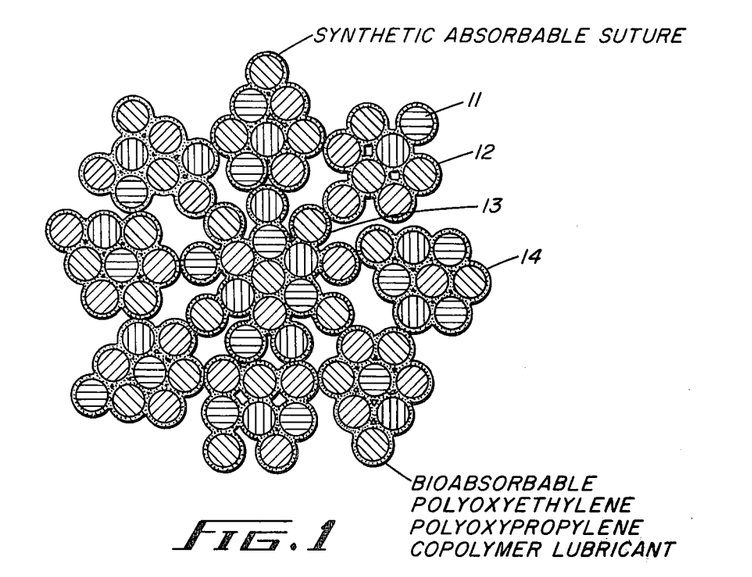
FIG. 1 is a cross-section of a synthetic absorbable suture having on the surface thereof a bioabsorbable polyoxyethylene polyoxypropylene copolymer lubricant.
Figure 2:
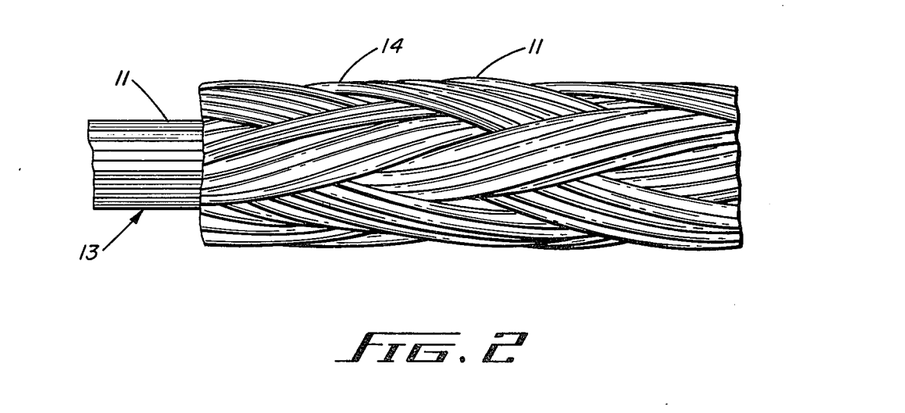
FIG. 2 is a drawing of a suture showing the parallel filaments in the core and the braided sheath. The lubricant coating appears on the surface.

The drawings are diagrammatic and representative. The filaments 11 of the synthetic bioabsorbable suture are at best some what jumbled in actual configuration but are illustrated as patterned in a somewhat idealized style. The coating 12 of the lubricant bioabsorbable polyoxyethylene-polyoxypropylene copolymer is shown much exaggerated. At a level of from 0.1 to 25 percent, the coating would be so thin as to merely be represented by a blurred line if to accurate scale.

In FIG. 2 the core 13 of the braided suture consists of parallel filaments and the sheath 14 consists of a plurality of filaments, typically braided in configuration. The type of braid shown is representative and diagrammatic. The visability and appearance of the coating varies depending upon the observational technique used to inspect the suture.

The coating 12 in part may bridge the gap between the individual filaments in the finished suture. Depending upon the quantity of coating used, the bridging may be more or less complete but complete filling is not necessary. If the coating level is increased, knot run-down continues to be improved, but knot security is compromised.

EXAMPLE 1

Run Down and Chatter Test

A set of 2/0 USP XIX (diameter 0.339 mm, maximum) polyglycolic acid sutures braided from a 2 denier per filament extrusion, was coated with 7 levels of Pluronic F-68 and a blank, that is no coating, then subjected to a square knot run-down test.

In this test, the suture is tied with a square knot around a cylinder with a 4 inch periphery. The loop thus formed is slipped off the cylinder and placed in the testing machine jaws. The knot is subjected to running-down by pulling on the original free ends in a testing machine which records the pull on a chart as the knot travels down the suture. There is some chatter or variation in knot run-down tension as the knot travels down the suture. This is graphically plotted. Out of a set of runs with various coating levels, the fraction is indicated in which the maximum force for the knot run-down is within the separate ranges given in the table. All of the knots for coated sutures ran down the full length of the suture without breaking. The knot breaking strength of the suture braid was in a range of 7 to 8 pounds. For uncoated braid, the knot locked up and the suture broke in 9 out of 10 tests.

TABLE III

Knot Run-Down on 2/0 Polyglycolic Acid Sutures with Pluronic F-68 Lubricant

| Coating Level (percent) | Fraction of trials where maximum resistance was: | | | | | | |
|---|---|---|---|---|---|---|---|
| | 0 – 1 | 1 – 2 | 2 – 3 | 3 – 4 | 4 – 5 | 5 – 6 | 6 – 7 lbs. |
| 0.0 | broke before run-down in 9 out of 10. | | | | | | |
| 1.9 | | | | 2/10 | 2/10 | 4/10 | 2/10 |
| 2.8 | | | 2/10 | 3/10 | 2/10 | 3/10 | |
| 3.9 | | 1/10 | | 1/10 | 4/10 | 2/10 | 2/10 |
| 5.0 | | 3/10 | 2/10 | 2/10 | 2/10 | 1/10 | |
| 6.2 | | 2/10 | 3/10 | 2/10 | 3/10 | | |
| 7.4 | 3/11 | 1/11 | 4/11 | 3/11 | | | |
| 8.0 | 5/10 | 2/10 | | 3/10 | | | |

The maximum force for rundown decreases steadily with increasing level, Lower coating levels on a different batch of braid showed

| 0.51% | 1/10 | 2/10 | 2/10 | 3/10 | 2/10 | | |
| 1.09% | 5/10 | 1/10 | 3/10 | 1/10 | | | |
| 1.53% | 5/10 | | 1/10 | 1/10 | 1/10 | 1/10 | 1/10 |

For these coatings, the braid was run through a solution of Pluronic F-68 at a concentration of about twice the percentage of coating on the suture in chloroform.

With other braid constructions and other sizes, the relative ease of knot run-down may be greater or less for the same quantity of coating, or conversely the quantity of the coating may be adjusted to give the desired knot run-down values.

The quantity of the Pluronic in the solvent may be varied, and solvents other than chloroform may be used.

Other organic solvents such as methyl alcohol, ethyl alcohol, isopropyl alcohol, methylene chloride, warm xylene (about 60° C.), tetrahydrofuran, acetone, dimethylformamide, dimethyl sulfoxide, mixtures thereof, and other similar solvents for the lubricant may be used for coating. Flowing the solution onto a moving strand, and letting the surplus drip off is another useful coating technique.

A small amount of water increases the solubility of the lubricants, and aids in coating, but the time of contact with water of the suture should be minimized so that if moisture is present in the coating system, the sutures should be dried and desiccated promptly.

In general it is more convenient to use the solvent coating system at levels below 10 percent pick-up and use a heated die at above about 10 percent pick-up.

EXAMPLE 2

A series of runs was made using a coating of two commercial Pluronics F-68 and F-127 on 2/0 size sutures of 6 dpf braided absorbable polyglycolic acid sutures. The coatings were applied by a solution of the Pluronic in chloroform. The concentration of the Pluronic in the solution used for coating is approximately twice that obtained in the braid. A solution containing about 2.8% Pluronic F-68 in chloroform results in about 1.4% Pluronic F-68 on the braid. An adjustment in concentration can be made to secure any desired level. The strand being coated was braided for a 2/0 size suture using a 6 denier per filament extrusion of polyglycolic acid. An uncoated suture strand of the same lot was used as a control. A standard ATLAB yarn Friction Tester Model CS-151-026, Custom Scientific Instruments, Inc. Whippany, New Jersey 07981, with a Hewlett Packard Model 321 dual channel amplifier recorder was used to record the tension of the strand feeding into the tester, and coming out of the yarn tester. The chatter factor is the ratio of maximum pull ($T_3$) to the feed tension ($T_1$) minus the minimum pull ($T_2$) to the feed tension, i.e. $(T_3/T_1) - (T_2/T_1)$. The values for friction are of $(T_2/T_1)$ to start slipping.

The values of particular interest are the ratios and percent reduction. With other types of test devices, the numerical values may change, but the relative ratios as an index of improvement are analogous.

In this test, an uncut strand, coated as indicated, was used for the test. For use as a suture, such strand is cut to length, needled, packaged and sterilized using conventional techniques. The friction and chatter is more readily measured on continuous lengths.

Reduction in static friction, chatter and the coefficient of friction are shown for typical coating levels, and sutures in Table IV.

Tests on knot security are dependent on the exact technique of tying knots.

A representative and typical run on knot security showed for a series of tests on size 2/0 polyglycolic acid sutures of 2 denier per filament construction with 4.79% of Pluronic® F-68 coated thereon and different knots, the force in pounds to slip knots or break without slipping to be:

| Run | Square Knot | Square + 1 Throw | Square + 2 Throws | Surgeons Knot | Surgeons + 1 Throw | Surgeons + 2 Throws |
|---|---|---|---|---|---|---|
| 1 | 1.70 | 2.95 | Broke | Broke | 7.50 | Broke |
| 2 | 2.05 | 3.90 | Broke | 6.15 | 5.15 | Broke |
| 3 | 4.20 | 4.05 | Broke | 3.70 | Broke | Broke |
| 4 | 0.70 | 3.40 | Broke | Broke | 3.35 | Broke |
| 5 | 3.95 | Broke | Broke | 1.40 | Broke | Broke |
| Average | 2.54 | — | — | — | — | — |

EXAMPLE 3

A series of runs, including blank, were made with solutions of the Pluronic® R bioabsorbable lubricant copolymers in chloroform, using the procedures of Example II. The following Table V shows the improvement obtained in chatter and friction with a series of polymers and concentrations.

TABLE IV
POLYGLYCOLIC ACID BRAID Size 2/0

| Run No. | Pluronic Coating | Level % | Static Friction | % Reduction | Chatter Factor | % Reduction | Coeff. of Friction $\times 10^{-2}$ | % Reduction |
|---|---|---|---|---|---|---|---|---|
| 1 | Blank | 0 | 3.11 | | 0.50 | | 6.109 | |
| 2 | Blank | 0 | 3.29 | | 0.60 | | 6.284 | |
| 3 | F-68 | 1.39 | 2.78 | 13.1 | 0.30 | 45.5 | 5.766 | 7.0 |
| 4 | F-68 | 1.93 | 2.55 | 20.3 | 0.19 | 65.5 | 5.468 | 11.8 |
| 5 | F-68 | 4.44 | 2.54 | 20.6 | 0.31 | 43.6 | 4.900 | 20.9 |
| 6 | F-68 | 7.29 | 2.70 | 15.6 | 0.33 | 40.0 | 5.084 | 17.9 |
| 7 | F-68 | 8.09 | 2.59 | 19.1 | 0.25 | 54.6 | 5.424 | 12.5 |
| 8 | F-127 | 1.38 | 2.55 | 20.3 | 0.33 | 40.0 | 4.938 | 20.3 |
| 9 | F-127 | 1.57 | 2.63 | 17.8 | 0.24 | 56.4 | 5.539 | 10.6 |
| 10 | F-127 | 2.56 | 2.97 | 7.2 | 0.27 | 50.9 | 6.104 | 1.50 |
| 11 | F-127 | 5.37 | 2.76 | 13.8 | 0.32 | 41.8 | 5.689 | 8.2 |
| 12 | F-127 | 5.62 | 2.82 | 11.9 | 0.40 | 27.3 | 5.617 | 9.4 |
| 13 | F-127 | 5.62 | 2.87 | 10.3 | 0.29 | 47.3 | 6.007 | 3.1 |
| 14 | F-127 | 8.14 | 2.81 | 12.2 | 0.29 | 47.3 | 5.891 | 4.9 |
| 15 | F-127 | 9.83 | 2.74 | 14.4 | 0.29 | 47.3 | 5.621 | 9.3 |

TABLE V
POLYGLYCOLIC ACID BRAID
Pluronic® Size 2/0 - 6 denier per filament

| Braid | Run | Coating | Level (%) | Static Friction | (%) Reduction | Chatter Factor | (%) Reduction | Coeff. of Friction $\times 10^{-2}$ | (%) Reduction |
|---|---|---|---|---|---|---|---|---|---|
| Uncoated | 16 | | | 3.92 | | 0.31 | | 8.189 | |
| Uncoated | 17 | | | 3.45 | | 0.21 | | 7.503 | |
| Uncoated | 18 | | | 2.87 | | 0.27 | | 6.083 | |
| Uncoated | 19 | | | 2.87 | | 0.18 | | 6.300 | |
| 10297B | 20 | 10R8 | 2.05 | 2.51 | 23.4 | 0.28 | | 5.077 | 28 |
| 10297B | 21 | 10R8 | 3.00 | 2.33 | 28.9 | 0.16 | 34.1 | 4.932 | 31 |
| 10297B | 22 | 10R8 | 3.96 | 2.31 | 29.5 | 0.21 | 13.6 | 4.753 | 33 |
| 10297B | 23 | 10R8 | 5.31 | 2.41 | 26.5 | 0.23 | 5.4 | 4.962 | 30 |
| 10297B | 24 | 10R8 | 7.49 | 2.39 | 27.1 | 0.25 | | 4.843 | 32 |
| 10297B | 25 | 25R8 | 2.55 | 2.34 | 28.6 | 0.16 | 34.1 | 4.962 | 30 |
| 10297B | 26 | 25R8 | 3.85 | 2.40 | 26.8 | 0.15 | 38.3 | 5.162 | 27 |
| 10297B | 27 | 25R8 | 6.29 | 2.23 | 32.0 | 0.15 | 38.3 | 4.662 | 34 |
| 10297B | 28 | 25R8 | 7.15 | 2.31 | 29.5 | 0.13 | 46.5 | 4.990 | 30 |
| 10297B | 29 | 25R8 | 8.74 | 2.37 | 27.7 | 0.11 | 54.7 | 5.175 | 27 |
| 10297B | 30 | 31R4 | 2.18 | 2.53 | 22.8 | 0.15 | 38.3 | 5.520 | 22 |
| 10297B | 31 | 31R4 | 3.42 | 2.53 | 22.8 | 0.17 | 30.0 | 5.466 | 23 |
| 10297B | 32 | 31R4 | 4.51 | 2.57 | 21.6 | 0.14 | 42.4 | 5.652 | 23 |
| 10297B | 33 | 31R4 | 5.53 | 2.61 | 20.4 | 0.17 | 30.0 | 5.705 | 20 |
| 10297B | 34 | 31R4 | 7.26 | 2.51 | 23.4 | 0.11 | 54.7 | 5.782 | 19 |
| 10297B | 35 | 17R8 | 2.12 | 2.45 | 25.3 | 0.19 | 21.8 | 5.218 | 27 |
| 10297B | 36 | 17R8 | 3.13 | 2.45 | 25.3 | 0.25 | | 5.019 | 30 |
| 10297B | 37 | 17R8 | 5.02 | 2.33 | 28.9 | 0.20 | 17.7 | 4.782 | 33 |
| 10297B | 38 | 17R8 | 6.32 | 2.36 | 28.0 | 0.25 | | 4.723 | 34 |
| 10297B | 39 | 17R8 | 8.60 | 2.33 | 28.9 | 0.15 | 38.3 | 4.962 | 30 |

EXAMPLE IV

A braided polyglycolic acid strand, of a size to form a 2/0 USP suture is dipped in a 10% solution of Pluronic F-68 in chloroform, and dried. The pick-up is about 5% by weight of the weight of the strand itself.

The dried coated strand is cut into 54" segments, needled, packaged, sterilized and dried in accordance with conventional procedures.

The thus prepared sutures were used in surgical procedures. When used to approximate tissue at a wound, a suture is placed in an appropriate location, and tied with a square knot. The square knot readily ran down to pull the edges of the wound to the degree of tightness desired by the using surgeon. The suture shows low tissue drag, and excellent knot run down. When a knot is at a desired final location, three additional squared throws are placed to secure the knot. Knots buried in tissue have the lubricant bioabsorbable copolymer removed from the suture surface within 48 hours, which gives additional knot security. The suture itself maintains tissue retaining strength for at least 15 days, and is substantially absorbed in 90 days.

Whereas exemplified and tested with square knots, the ease of knot run-down and reduced tissue drag are useful in most suture placements and for knot retention. The amount of coating, and the relative values for knot run-down and reduced tissue drag, is variable to suit the requirement of a particular surgical situation.

The needling, packaging and sterilizing of the coated sutures is in accordance with conventional procedures.

We claim:

1. An absorbable surgical suture having improved knot run-down characteristics and reduced tissue drag comprising a polyfilamentary synthetic absorbable polymer strand having thereon a thin lubricating coating of a lubricating absorbable copolymer comprising polyoxyethylene blocks and polyoxypropylene blocks to aid run-down and handleability, said bioabsorbable copolymer having a molecular weight such that it is pasty to solid at 25° C.

2. The suture of claim 1 in which the lubricating bioabsorbable polymer has the formula:

$$R[(CH_2CHO)_n(CH_2CHO)_mH]_c$$

where one of $R_1$ and $R_2$ is methyl and the other hydrogen, and $n$ and $m$ are sufficiently large that the compound is pasty to solid at 25° C., R is the residue of a relatively low molecular weight reactive hydrogen compound having from 2 to about 6 reactive hydrogen atoms and having not over 6 carbon atoms in said compound, and $c$ is the number of reactive hydrogens on the compound forming R.

3. The suture of claim 1 in which the lubricating bioabsorbable copolymer has effectively the formula:

$$H(OCH_2CH_2)_x(OCHCH_2)_y(OCH_2CH_2)_zOH$$

where $x$, $y$ and $z$ are sufficiently large that the lubricating bioabsorbable copolymer is pasty to solid at 25° C.

4. The suture of claim 3 in which the lubricating bioabsorbable copolymer has a molecular weight of about 8350 and $x$ and $z$ are about 75 and $y$ about 30, and the melting point is about 52° C.

5. The suture of claim 1 in which the lubricating bioabsorbable copolymer has effectively the formula:

$$H(OCHCH_2)_n(OCH_2CH_2)_m(OCHCH_2)_oOH$$

where $n$, $m$ and $o$ are sufficiently large that the lubricating bioabsorbable copolymer is pasty to solid at 25° C.

6. The suture of claim 1 in which the lubricating bioabsorbable copolymer has effectively the formula:

where $R_3$ is $$-(CH_2CHO)_q(CH_2CH_2O)_rH.$$

where $q$ and $r$ are sufficiently large that the lubricating bioabsorbable copolymer is pasty to solid at 25° C.

7. The suture of claim 1 in which the synthetic absorbable polymer strand is of a tissue absorbable polymer subject to hydrolytic degradation to non-toxic tissue compatible absorbable components, and which polymer has glycolic acid ester linkages.

8. The suture of claim 3 in which the synthetic absorbable polymer strand is of a tissue absorbable polymer subject to hydrolytic degradation to non-toxic tissue compatible absorbable components, and which polymer has glycolic acid ester linkages.

9. The suture of claim 4 in which the synthetic absorbable polymer strand is of a tissue absorbable polymer subject to hydrolytic degradation to non-toxic tissue compatible absorbable components, and which polymer has glycolic acid ester linkages.

10. The suture of claim 7 in which the tissue absorbable polymer is polyglycolic acid.

11. The suture of claim 8 in which the tissue absorbable polymer is polyglycolic acid.

12. The suture of claim 9 in which the tissue absorbable polymer is polyglycolic acid.

13. The suture of claim 1 in which the lubricating coating is about 0.1 to 25 percent by weight of the lubricating bioabsorbable copolymer of the weight of the uncoated strand forming the suture, whereby both chatter and friction are reduced sufficiently that a square knot is movable on the suture with control of a wound edge.

14. The suture of claim 2 in which the lubricating coating is about 0.1 to 25 percent by weight of the lubricating bioabsorbable copolymer of the weight of the uncoated strand forming the suture, whereby both chatter and friction are reduced sufficiently that a square knot is movable on the suture with control of a wound edge.

15. The suture of claim 3 in which the lubricating coating is about 0.1 to 25 percent by weight of the lubricating bioabsorbable copolymer of the weight of the uncoated strand forming the suture, whereby both chatter and friction are reduced sufficiently that a square knot is movable on the suture with control of a wound edge.

16. The suture of claim 4 in which the lubricating coating is about 0.1 to 25 percent by weight of the lubricating bioabsorbable copolymer of the weight of the uncoated strand forming the suture, whereby both chatter and friction are reduced sufficiently that a square knot is movable on the suture with control of a wound edge.

17. The suture of claim 7 in which the lubricating coating is about 0.1 to 25 percent by weight of the lubricating bioabsorbable copolymer of the weight of the uncoated strand forming the suture, whereby both chatter and friction are reduced sufficiently that a square knot is movable on the suture with control of a wound edge.

18. The suture of claim 8 in which the lubricating coating is about 0.1 to 25 percent by weight of the lubricating bioabsorbable copolymer of the weight of the uncoated strand forming the suture, whereby both chatter and friction are reduced sufficiently that a square knot is movable on the suture with control of a wound edge.

19. The suture of claim 9 in which the lubricating coating is about 0.1 to 25 percent by weight of the lubricating bioabsorbable copolymer of the weight of the uncoated strand forming the suture, whereby both chatter and friction are reduced sufficiently that a square knot is movable on the suture with control of a wound edge.

20. The suture of claim 10 in which the lubricating coating is about 0.1 to 25 percent by weight of the lubricating bioabsorbable copolymer of the weight of the uncoated strand forming the suture, whereby both chatter and friction are reduced sufficiently that a square knot is movable on the suture with control of a wound edge.

21. The suture of claim 11 in which the lubricating coating is about 0.1 to 25 percent by weight of the lubricating bioabsorbable copolymer of the weight of the uncoated strand forming the suture, whereby both chatter and friction are reduced sufficiently that a square knot is movable on the suture with control of a wound edge.

22. The suture of claim 12 in which the lubricating coating is about 0.1 to 25 percent by weight of the lubricating bioabsorbable copolymer of the weight of the uncoated strand forming the suture, whereby both chatter and friction are reduced sufficiently that a square knot is movable on the suture with control of a wound edge.

23. A method of closing a wound in living tissue which comprises: sewing edges of a wound in living tissue with the sterile absorbable surgical suture of claim 1,
   tying the suture into a square knot,
   running down the square knot to approximate the tissues in a desired location,
   placing additional throws on the square knot, and
   within less than about 48 hours bioabsorbing and removing the lubricant absorbable copolymer from the suture thereby increasing knot security and,
   leaving the absorbable surgical suture in living tissue until the suture strand is absorbed by living tissue during the healing process, the suture providing useful tissue retention strength for at least 15 days and absorption being substantially complete within 90 days.

* * * * *

UNITED STATES PATENT OFFICE
CERTIFICATE OF CORRECTION

Patent No. 4,047,533     Dated September 13, 1977

Inventor(s) Vincent Anthony Perciaccante et al.

It is certified that error appears in the above-identified patent and that said Letters Patent are hereby corrected as shown below:

Column 5, lines 50 - 54, the formula should appear as shown below:

$$H(OCH_2CH_2)_x(\underset{\underset{CH_3}{|}}{O\overset{}{C}HCH_2})_y(OCH_2CH_2)_zOH$$

Column 6, lines 1 - 5, the formula should appear as shown below:

$$H(\underset{\underset{CH_3}{|}}{O\overset{}{C}HCH_2})_n(OCH_2CH_2)_m(\underset{\underset{CH_3}{|}}{O\overset{}{C}HCH_2})_oOH$$

Columns 7 and 8, under the heading "Table I - continued" delete "M. W. polyethylene units of m blocks" and add -- M. W. of polyoxyehtylene units of m block --.

Same Table I - continued, on the line "REVERSE PLURONIC" shift "M. W. polyethylene units of m block" from the fourth column to the third column.

Same Table I - continued, on the line "REVERSE PLURONIC" shift "Units of" from between the seventh and eighth columns to "n and o" the seventh column.

UNITED STATES PATENT OFFICE
CERTIFICATE OF CORRECTION

Patent No. 4,047,533         Dated September 13, 1977

Inventor(s) Vincent Anthony Perciaccante et al.

It is certified that error appears in the above-identified patent and that said Letters Patent are hereby corrected as shown below:

Same Table I - continued, on the line "TETRONIC" delete "Approximate Polyoxypropylene" and insert -- Approximate % Polyoxyproylene --.

Signed and Sealed this

Eighteenth Day of April 1978

[SEAL]

Attest:

RUTH C. MASON
Attesting Officer

LUTRELLE F. PARKER
Acting Commissioner of Patents and Trademarks